US010416119B2

(12) United States Patent
Katta

(10) Patent No.: US 10,416,119 B2
(45) Date of Patent: Sep. 17, 2019

(54) MEASUREMENT METHOD OF SPECIMEN LIQUID AND SPECIMEN LIQUID SENSOR

(71) Applicant: KYOCERA CORPORATION, Kyoto (JP)

(72) Inventor: Hiroshi Katta, Kashihara (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/553,807

(22) PCT Filed: Feb. 29, 2016

(86) PCT No.: PCT/JP2016/056143
§ 371 (c)(1),
(2) Date: Aug. 25, 2017

(87) PCT Pub. No.: WO2016/137009
PCT Pub. Date: Sep. 1, 2016

(65) Prior Publication Data
US 2018/0074017 A1 Mar. 15, 2018

(30) Foreign Application Priority Data

Feb. 27, 2015 (JP) ................................. 2015-038400

(51) Int. Cl.
| | | |
|---|---|---|
| *G01N 29/024* | (2006.01) | |
| *G01N 29/02* | (2006.01) | |
| *H03H 3/08* | (2006.01) | |
| *G01N 29/30* | (2006.01) | |
| *G01N 33/53* | (2006.01) | |
| *G01N 33/543* | (2006.01) | |

(Continued)

(52) U.S. Cl.
CPC .......... *G01N 29/024* (2013.01); *G01N 29/02* (2013.01); *G01N 29/022* (2013.01);
(Continued)

(58) Field of Classification Search
CPC .......... G01N 29/024; G01N 33/54373; G01N 29/022; G01N 29/30; G01N 29/2468;
(Continued)

(56) References Cited

U.S. PATENT DOCUMENTS

| 8,636,953 B2 | 1/2014 | Katta |
|---|---|---|
| 2006/0019330 A1 | 1/2006 | Lakshmi et al. |

(Continued)

FOREIGN PATENT DOCUMENTS

| CN | 1922481 | 2/2007 |
|---|---|---|
| JP | 2007-517227 A | 6/2007 |

(Continued)

OTHER PUBLICATIONS

Extended European Search Report dated Dec. 18, 2017 in corresponding EP Patent Application No. 16755753.7.

(Continued)

*Primary Examiner* — Melanie Brown
(74) *Attorney, Agent, or Firm* — Duane Morris LLP

(57) ABSTRACT

A measurement method of a specimen liquid includes preparing a sensor chip comprising a reference SAW element and a detection SAW element have a relationship of an expression: $t \cdot V < L$, where t, V and L denote is as defined in the specification; causing the specimen liquid to flow in order from either one of the reference SAW element and the detection SAW element: calculating a change with time of a phase difference $\Delta\theta$ between a phase $\theta\text{ref}$ in the reference SAW element and a phase $\theta\text{test}$ in the detection SAW element; and measuring a detection target from a starting point which is a point in time at an extreme value or later in the change with time of the phase difference $\Delta\theta$.

8 Claims, 11 Drawing Sheets

(51) Int. Cl.
  *G01N 29/24* (2006.01)
  *G01N 29/44* (2006.01)

(52) U.S. Cl.
  CPC ..... *G01N 29/2462* (2013.01); *G01N 29/2468* (2013.01); *G01N 29/30* (2013.01); *G01N 29/4436* (2013.01); *G01N 33/5308* (2013.01); *G01N 33/54373* (2013.01); *H03H 3/08* (2013.01); *G01N 2291/012* (2013.01); *G01N 2291/0255* (2013.01); *G01N 2291/048* (2013.01); *G01N 2291/0423* (2013.01)

(58) Field of Classification Search
  CPC .......... G01N 29/4436; G01N 29/2462; G01N 33/5308; G01N 29/02; H03H 3/08
  See application file for complete search history.

(56) References Cited

U.S. PATENT DOCUMENTS

| | | | |
|---|---|---|---|
| 2007/0190662 A1* | 8/2007 | Baetzold | B01L 3/502746 436/166 |
| 2007/0245810 A1 | 10/2007 | Carter et al. | |
| 2007/0281369 A1 | 12/2007 | Carter et al. | |
| 2009/0320574 A1 | 12/2009 | Yamada et al. | |
| 2012/0040473 A1* | 2/2012 | Mansson | G01N 29/022 436/501 |
| 2013/0259746 A1* | 10/2013 | Katta | G01N 29/032 422/68.1 |
| 2016/0195498 A1 | 7/2016 | Katta | |

FOREIGN PATENT DOCUMENTS

| | | |
|---|---|---|
| JP | 2008120511 A | 5/2008 |
| JP | 2014112084 A | 6/2014 |
| WO | 2014/192393 A1 | 12/2014 |

OTHER PUBLICATIONS

International Search Report dated May 17, 2016, in corresponding International Application No. PCT/JP2016/056143.

Yatsuda, H. et al., "Sh-Saw Biosensor for Poct", The Research Committee on Electronic Circuits of the Institute of Electrical Engineers of Japan (IEEJ), EM symposium, May 2011, 2 pages. English translation provided.

* cited by examiner $\Delta \theta = \theta\, ref - \theta\, test$

US 10,416,119 B2

MEASUREMENT METHOD OF SPECIMEN LIQUID AND SPECIMEN LIQUID SENSOR

TECHNICAL FIELD

The present invention relates to a measurement method of a specimen liquid for measuring a specific component to be detected contained in a specimen liquid, and a specimen liquid sensor used therefor.

BACKGROUND ART

In general, a specimen liquid sensor unit (specimen liquid sensor apparatus) is known, which includes a specimen liquid sensor holding a specimen liquid and capable of converting an input electric signal in accordance with characteristics or components of a specimen liquid and a reader transmitting and receiving an electric signal to and from the specimen liquid sensor.

As a specimen liquid sensor, a SAW sensor of which size can be reduced attracts attention, because the price of the SAW sensor can be reduced through mass production, and the detection circuit can be realized with a simple electric circuit (Non Patent Document 1). The SAW sensor has an input electrode for generating a surface acoustic wave (SAW) from an electric signal and an output electrode for receiving the SAW on the upper surface of the substrate. In the SAW sensor, a metal film having an antigen fixed on the surface is arranged between these electrodes, and the SAW sensor analyzes the output signal resulting from bonding of the antigen and the antibody and find the component of the specimen liquid based on the change in the phase characteristics of the SAW.

RELATED ART DOCUMENT

Non-Patent Document

Non-Patent Document 1: Hiromi Yatsuda et al., "SH-SAW Biosensor for POCT", The Research Committee on Electronic Circuits of the Institute of Electrical Engineers of Japan (IEEJ), EM symposium, 2011.5

SUMMARY OF THE INVENTION

A measurement method of a specimen liquid according to an embodiment of the present invention comprises preparing a sensor chip comprising a plurality of SAW elements located along a flow direction of the specimen liquid on an upper surface of a piezoelectric substrate, wherein a reference SAW element and a detection SAW element of the plurality of SAW elements have a relationship of an expression: $t \cdot V < L$ (where t denotes a data reading interval time from both of the SAW elements, and V denotes a flow rate of the specimen liquid, and L denotes a distance between both of the SAW elements); causing the specimen liquid to flow in order from either one of the reference SAW element and the detection SAW element; calculating a change with time of a phase difference $\Delta\theta$ which is a difference between a phase $\theta$ref of a surface acoustic wave in the reference SAW element and a phase $\theta$test of a surface acoustic wave in the detection SAW element; and measuring a detection target from a starting point which is a point in time at an extreme value or later in the change with time of the phase difference $\Delta\theta$.

A specimen liquid sensor according to an embodiment of the present invention includes a base and a sensor chip located on an upper surface of the base. The sensor chip includes a piezoelectric substrate located on the upper surface of the base and a plurality of SAW elements located in a flow direction of the specimen liquid on the upper surface of the piezoelectric substrate, and two SAW elements of the plurality of SAW elements have a relationship of an expression: $t \cdot V < L$ (where t denotes a data reading interval time from both of the SAW elements, V denotes a flow rate of the specimen liquid, and L denotes a distance between both of the SAW elements).

EFFECTS OF THE INVENTION

According to the measurement method of the specimen liquid of the embodiment of the present invention, the reference SAW element and the detection SAW element have the relationship of the expression mentioned above, and therefore, in the difference between the phase $\theta$ref of the surface acoustic wave in the reference SAW element and the phase $\theta$test of the surface acoustic wave in the detection SAW element, i.e., the change with time of the phase difference $\Delta\theta$, the extreme value (the maximum value or the minimum value) emerges. This extreme value indicates a point in time when the specimen liquid flowing through one SAW element reaches the other SAW element. Therefore, the extreme value or later is adopted as the starting point of the signal from the specimen liquid sensor, and the detection target is measured by using the change with time at the extreme value or later, so that the measurement (concentration measurement and the like) of the detection target contained in the specimen liquid can be performed easily and accurately.

EMBODIMENTS FOR CARRYING OUT THE INVENTION

<Specimen Liquid Sensor>

First, a specimen liquid sensor according to one embodiment of the present invention will be described in details with reference to the drawings.

Figure 1:
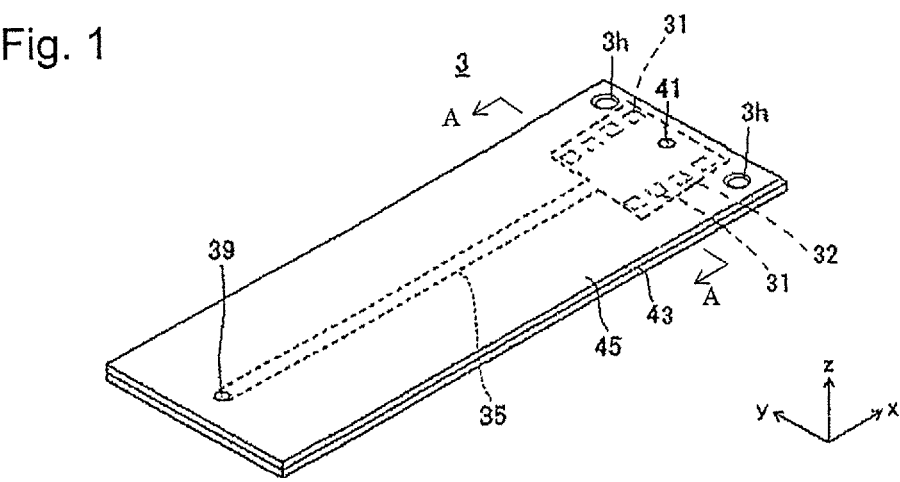
FIG. 1 is a perspective view illustrating a specimen liquid sensor according to one embodiment of the present invention.

FIG. 1 illustrates a specimen liquid sensor 3 according to the present embodiment. The specimen liquid sensor 3 has a base 43 and a cover 45 arranged on the base 43, and a flow path 35 is formed between the base 43 and the cover 45. A sensor chip 32 is formed at the tip of the flow path 35 on the upper surface of the base 43, and an external terminal 31 is formed on the lower surface of the base 43 to send data from the sensor chip 32.

The shape of the specimen liquid sensor 3 is roughly in the form of a plate as a whole, and, for example, the planar shape of the specimen liquid sensor 3 is a rectangle.

For example, the flow path 35 is formed to extend linearly in the longitudinal direction of the specimen liquid sensor 3 (x direction, direction from the portion exposed from the reader 5 to the portion sandwiched by the reader 5). Both ends of the flow path 35 extend to the outside of the specimen liquid sensor 3. One end of the flow path 35 is an inflow port 39 for taking specimen liquid. The other end of the flow path 35 is an exhaust port 41 for discharging air from the flow path 35 when the specimen liquid flows into the flow path 35. It should be noted that the inflow port 39 and the exhaust port 41 are preferably open to the upper surface of the specimen liquid sensor 3.

The flow path 35 is configured to guide the specimen liquid dropped into the flow port 39 (coming in contact with the flow port 39) toward the exhaust port 41 with capillary action. For example, the height (thickness, z direction) of the flow path 35 is configured to be relatively low, and wettability of at least one of the bottom surface and the ceiling surface is configured to be relatively high.

The height of the flow path 35 in the z direction is not particularly limited, and is preferably 50 μm to 0.5 mm. More preferably, the height of the flow path 35 in the z direction is about 50 μm from the viewpoint of reducing the amount of specimen liquid. It should be noted that when diluting of undiluted liquid such as blood is used as the specimen liquid, the amount of the specimen liquid is not necessarily reduced. The contact angle (wettability) of the specimen liquid (which may be represented by water) on the bottom surface and the ceiling surface of the flow path 35 is less than 90 degrees, and is more preferably less than 60 degrees.

In the present embodiment, the base 43 has insulating property. For example, the material of the base 43 may be resin or ceramic. The base 43 may be a multilayer board, such as those having a ground layer as a shield inside. It should be noted that, for example, the planar shape of the base 43 is similar to the planar shape of the entire specimen liquid sensor 3.

For example, the planar shape of the outer shape of the cover 45 is roughly the same as the planar shape of the entire specimen liquid sensor 3. On the lower surface of the cover 45, a groove is formed between the cover 45 and the base 43 to form the flow path 35. The cover 45 is formed so that the inflow port 39 and the exhaust port 41 described above pass through the cover 45 in the vertical direction. For example, the cover 45 is pasted to the base 43 with an adhesive.

For example, the cover 45 is made of an insulating material such as resin or ceramic. The entire cover 45 may be integrally formed of the same material. The cover 45 may be formed by stacking a plurality of layered members made of the same material or different materials. For example, the cover 45 may be composed of a layered member having a slit formed as the flow path 35 and a layered member arranged thereon and constituting the ceiling surface of the flow path 35.

At least one of the base 43 and the cover 45 is preferably made of a material having high hydrophilicity, applied with hydrophilic treatment, or applied with a hydrophilic film pasted thereon, in order to increase the wettability of the inner surface of the flow path 35 in at least the region constituting the flow path 35. For example, a hydrophilic film may be pasted to the base 43 in a region overlapping with the flow path 35. In this case, the hydrophilic film may be considered to be a part of the base 43. For example, as described above, in the case where the cover 45 is formed by stacking layered members, the upper layered member which closes the slit may be constituted by a hydrophilic film.

It should be noted that the entire specimen liquid sensor 3 preferably does not have flexibility. For example, at least one of the base 43 and the cover 45 preferably does not have flexibility.

Figure 2:
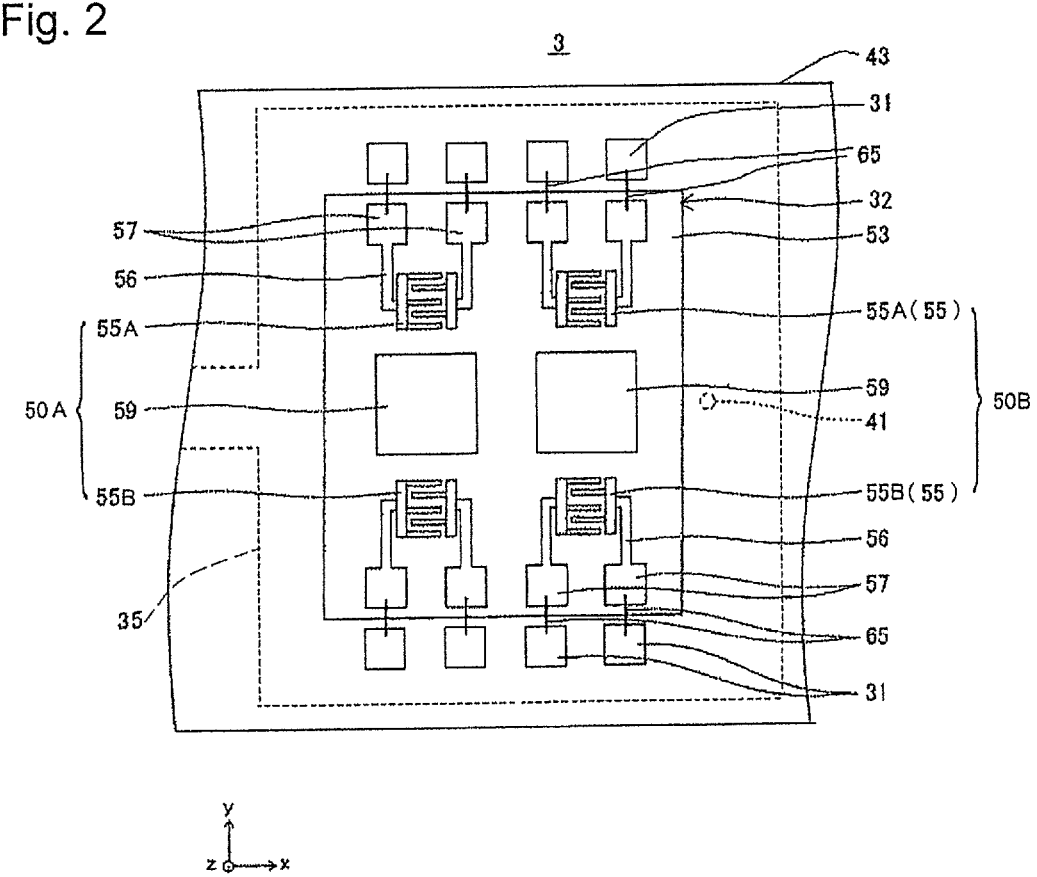
FIG. 2 is a plan view illustrating a part of the specimen liquid sensor of FIG. 1.

FIG. 2 is a schematic diagram illustrating a cross-sectional shape of the sensor chip 32 of the specimen liquid sensor 3, with cover 45 removed from the specimen liquid sensor 3.

In the specimen liquid sensor 3, the sensor unit 32 that detects the detection target contained in the specimen liquid passing through the flow path 35 is mounted on the upper surface of the base 43. The sensor unit 32 is a sensor chip which substantially converts a signal corresponding to the specimen liquid, and the base 43 and the cover 45 function as a package which contributes to improvement of the ease of handling of the sensor unit 32 and the like. Although not specifically shown, at least one of the lower surface of the cover 45 and the upper surface of the base 43 is formed with a recessed portion for accommodating the sensor unit 32.

The sensor unit 32 includes a piezoelectric substrate 53 and at least two SAW elements 50A, 50B located at positions along the flow direction of the specimen liquid on the upper surface of the piezoelectric substrate 53. The SAW elements 50A, 50B include a first IDT 55A which generates a surface acoustic wave (SAW) on the main surface of the piezoelectric substrate 53, a second IDT 55B located in the propagation path of the SAW to receive the SAW, a plurality of chip pads 57 provided for inputting an electric signal to the first IDT 55A or outputting an electric signal from the second IDT 55B, and a sensitive part 59 for changing the SAW according to the property or the component of the specimen liquid. For example, not only a metal film described later but also an insulating film (an oxide film, a nitride film, and the like) can be used as the sensitive part 59.

The piezoelectric substrate 53 is made of a single crystal substrate having a piezoelectric property such as, for example, monocrystalline lithium tantalate (LiTaO$_3$), monocrystalline lithium niobate (LiNbO$_3$), quartz. The planar shape and various dimensions of the piezoelectric substrate 53 may be appropriately set. For example, the thickness of the piezoelectric substrate 53 is 0.3 mm to 1.0 mm. The piezoelectric substrate 53 is arranged so that its principal plane is parallel to the base 43.

The first IDT 55A and the second IDT 55B (hereinafter simply referred to as "IDTs", which may not be distinguished from each other) are made of conductor layers located on the upper surface of the piezoelectric substrate 53. The first IDT 55A and the second IDT 55B are opposed to each other with the flow path 35 interposed therebetween. Each IDT 55 has a pair of comb tooth electrodes. Each comb tooth electrode has a bus bar and a plurality of electrode fingers extending from the bus bar. The pair of comb tooth electrodes are arranged so that a plurality of electrode fingers mesh with each other. The first IDT 55A and the second IDT 55B are spaced apart from each other in the propagation direction of the SAW and constitute a transversal type IDT.

The frequency characteristics can be designed by using, as parameters, the number of electrode fingers of IDT 55, the distance between adjacent electrode fingers, the intersection width of electrode fingers, and the like. The SAW excited by the IDT 55 include Rayleigh wave, Love wave, leaky wave, and the like, and any of them may be used. The sensor unit 32 uses, for example, Love wave.

In the SAW propagation direction (y direction), an elastic member may be provided outside of the first IDT 55A and the second IDT 55B to suppress the reflection of the SAW. For example, the frequency of the SAW can be set in a range of several megahertz (MHz) to several gigahertz (GHz). Particularly, if the frequency of the SAW is several hundred megahertz to 2 gigahertz, the sensor unit 32 is practical, and the size of the piezoelectric substrate 53 can be reduced, and further, the size of the sensor unit 32 can be reduced.

The chip pad 57 is connected to the IDT 55 via the chip wiring 56. For example, like the IDT 55, the chip pad 57 and the chip wire 56 are composed of conductor layers located on the upper surface of the piezoelectric substrate 53. The chip pad 57 connected to the first IDT 55A is located at the first IDT 55A at the side opposite to the second IDT 55B. The chip pad 57 connected to the second IDT 55B is located at the second IDT 55B at the side opposite to the first IDT 55A. The chip pad 57 preferably overlaps the IDT 55 as seen in the opposing direction (y direction) of the first IDT 55A and the second IDT 55 in order to reduce the arrangement range of the plurality of chip pads 57 in the x direction while securing a wide area of each chip pad 57.

For example, the IDT 55, the chip wire 56, and the chip pad 57 are made of gold, aluminum, an alloy of aluminum and copper, or the like. These electrodes may have a multilayer structure. In the case of a multilayer structure, for example, the first layer is made of titanium or chromium, and the second layer is made of aluminum or an aluminum alloy. These thicknesses thereof are, for example, 100 nm to 300 nm.

The upper surface of the piezoelectric substrate 53 may be covered with a protective film (not shown) from above the IDT 55 and the chip wire 56. The protective film contributes to the suppression of oxidation of the IDT 55 and the chip wire 56, and the like. The protective film is made of silicon oxide, aluminum oxide, zinc oxide, titanium oxide, silicon nitride, silicon, or the like. In the specimen liquid sensor 3, silicon dioxide (SiO$_2$) is used as the protective film. The protective film is formed on the entire upper surface of the piezoelectric substrate 53 so that, for example, the chip pad 57 is exposed. The thickness of the protective film (the height from the upper surface of the piezoelectric substrate 53) is more than the thickness of, for example, the IDT 55, and is 200 nm to 10 μm.

The sensitive part 59 is positioned between the first IDT 55A and the second IDT 55B on the piezoelectric substrate 53 or the protective film. The sensitive part 59 is located in the flow path 35. The sensitive part 59 has a two-layer structure including, for example, titanium and gold deposited on the titanium, or chrome and gold deposited on the chromium.

The SAW element 50A, which is one of the two SAW elements 50A, 50B, does not have, on the surface of the sensitive part 59, specific bonding substance bonding with the detection target included in the specimen liquid, and the SAW element 50B, which is the other of the two SAW elements 50A, 50B, includes specific bonding substance. Hereinafter, the SAW element 50A not having the specific bonding substance may be referred to as the reference SAW element 50A, and the SAW element 50B having the specific bonding substance may be referred to as the detection SAW element 50B.

By comparing the SAW element 50A and the SAW element 50B, the change of the SAW due to the bonding between the specimen liquid and the specific bonding substance can be measured as described later. Different kinds of specific bonding substances may be fixed on the metal film of the sensitive part 59 for different SAW elements, and different properties or components may be measured for the specimen liquid.

Both of the reference SAW element 50A and the detection SAW element 50B may have the specific bonding substance, in which case the densities of the specific bonding substance are made to be different between the SAW elements 50A and 50B. More specifically, the density of the specific bonding substance in the reference SAW element 50A may be lower than the density of the specific bonding substance in the detection SAW element 50B.

The two SAW elements 50A, 50B have the following relationship.

expression: $t \cdot V < L$ (where t denotes a data reading interval time from the two SAW elements 50A, 50B, V denotes a flow rate of the specimen liquid, and L denotes a distance between the two SAW elements 50A, 50B)

More specifically, for example, the above equation means that the distance for which the specimen liquid flows during the period from the first data reading to the second data reading is smaller than the distance between the SAW elements 50A and 50B. Therefore, the detection target contained in the specimen liquid can be measured as described later.

The detection SAW element 50B and the reference SAW element 50A may have different densities of specific bonding substances. More specifically, the density of the specific bonding substance in the reference SAW element 50A may be lower than the density of the specific bonding substance of the detection SAW element 50B.

The specific bonding substance includes an aptamer composed of nucleic acid and peptide, and the aptamer is fixed on the surface of the sensitive part 59.

When the specimen liquid comes into contact with the sensitive part 59 to which the aptamer is fixed, a specific target substance in the specimen liquid is bonded with the aptamer corresponding to the target substance, and the weight of the sensitive part 59 changes. As a result, there is a change in the phase characteristics and the like of the SAW propagating from the first IDT 55A to the second IDT 55B. Therefore, the properties or components of the specimen liquid can be found based on the change in the phase characteristics and the like.

An appropriate number of SAW elements made of combinations of the first IDT 55A, the second IDT 55B, and the sensitive part 59 may be provided in the flow path direction of the flow path 35 (the flow direction of the specimen liquid).

The method of mounting the sensor unit 32 on the base 43 may be appropriately adopted. In the present embodiment, the mounting method of the sensor unit 32 is a surface mounting using the bonding wire 65. When the specimen liquid sensor has a sensor chip, the mounting method of the sensor chip is not limited to the surface mounting using the wire bonding. For example, the mounting method may be a flip chip mounting using a bump, or a lead insertion mounting method in which a lead is inserted into a substrate.

In the sensor unit 32, the IDT 55 (the first IDT 55A and the second IDT 55B) is connected to the chip pad 57 via the chip wire 56, and this chip pad 57 is connected to the external terminal 31 via the bonding wire 65.

<Specimen Liquid Sensor Apparatus>

Figure 3A:
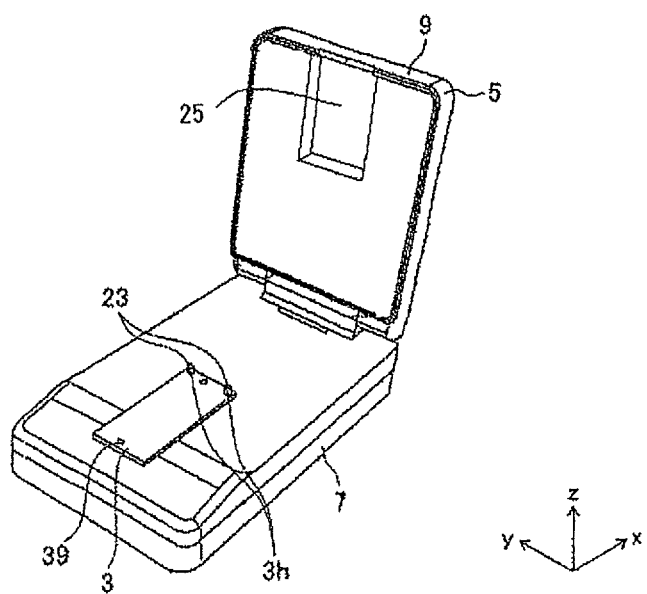
FIGS. 3(a) and 3(b) are perspective views illustrating the specimen liquid sensor apparatus with the specimen liquid sensor attached to the reader.

Subsequently, the specimen liquid sensor apparatus 1 equipped with specimen liquid sensor 3 will be hereinafter explained with reference to FIG. 3(*a*), FIG. 3(*b*), FIG. 4, and FIG. 5. FIG. 3(*a*) is a perspective view illustrating a specimen liquid sensor apparatus 1 (which may be hereinafter simply referred to as "apparatus 1") in the closed state. FIG. 3(*b*) is a perspective view illustrating a portion of the apparatus 1 in an open state and in a state before the specimen liquid sensor is mounted. FIG. 4 is a perspective view illustrating the apparatus 1 in the open state.

The apparatus 1 includes the reader 5 to which the specimen liquid sensor 3 is detachably attached. The reader 5 includes a first portion 7 (for example, fixed portion) and a second portion 9 (for example, movable portion) coupled to be able to transit (able to relatively move) between the open state as shown in FIG. 3 and the closed state as shown in FIG. 4, and includes a connection component 2 including connection terminals 21 located on an upper surface of the first portion 7, positioning pins 23, and a terminal holding member 29 (a contact unit). Both of the first portion 7 and the second portion 9 constitute the outline of the reader 5.

The reader 5 is configured so that in the closed state, the connection terminal 21 located on the upper surface of the first portion 7 is connected to the external terminal 31 of the specimen liquid sensor 3 detachably sandwiched between the upper surface of the first portion 7 and the lower surface of the second portion 9, and the reader 5 inputs an electric signal from the connection terminal 21 to the external terminal 31, and receives an electric signal that is output from the specimen liquid sensor 3. At this time, the specimen liquid sensor 3 which sucks and accommodates the specimen liquid changes the electric signal received by the specimen liquid sensor 3 according to the properties or the component of the specimen liquid and outputs the changed electric signal.

As shown in FIG. 1 and FIG. 2, the external terminal 31 is provided on the lower surface side (at the side of the first portion 7) of the specimen liquid sensor 3 so that the external terminal 31 comes into contact with the connection terminal 21 on the first portion 7 when the specimen liquid sensor 3 is sandwiched by the reader 5.

For example, the number and the arrangement of such external terminals 31 are such that the external terminals 31 are arranged along flow path 35 on both sides in a width direction of flow path 35 in the present embodiment, but the present embodiment is not limited thereto, and the number and arrangement of the external terminals 31 are appropriately set according to the circuit configuration inside of the specimen liquid sensor 3 and the like.

In the open state, the second portion 9 moves away from the first portion 7 with respect to the closed state (FIG. 3(*a*)). In the closed state, the second portion 9 overlaps on the upper surface of the first portion 7 and faces the first portion 7 (FIG. 4). Therefore, when the reader 5 is in the open state, the surfaces of the first portion 7 and the second portion 9 facing each other are exposed to the outside. When the specimen liquid sensor 3 is placed on the exposed upper surface of the first portion 7, and the second portion 9 is displaced (moved) to make it into a closed state, the specimen liquid sensor 3 is sandwiched between the first portion 7 and the second portion 9 and is attached to the reader 5. When the specimen liquid sensor 3 is to be removed from reader 5, the above procedure may be performed in the opposite order.

As shown in FIG. 3 and FIG. 4, for example, the mode of transition (opening and closing mechanism) between the closed state and the open state of the first portion 7 and the second portion 9 may be a so-called folding type, i.e., the closed state and the open state of the first portion 7 and the second portion 9 are connected rotatably around the rotation axis. For example, as shown in FIG. 4, a first protruding portion 9*a* protruding in a direction (z direction) opposed to the second portion 9 in the closed state is formed at one end of the first portion 7. On the other hand, a notch 9*b* in which the first protrusion portion 9*a* is accommodated is formed at one end of the second portion 9. In other words, a pair of second protrusion portions 9*c* constituting the notch 9*b* are formed at the one end of the second portion 9. A hinge member (not shown) is inserted in the first protruding portion 9*a* and the second protruding portion 9*c* in the y direction, so that the first portion 7 and the second portion 9 are rotatably connected to each other around a rotation axis parallel to the y direction. A known opening and closing mechanism for mobile phones or notebook type personal computers may be used for such opening and closing mechanism.

The opening and closing mechanism of the first portion 7 and the second portion 9 is not limited to the case where the ends are connected to each other or fixed using a hinge member or the like as described above. Alternatively, the opening and closing mechanism of the first portion 7 and the second portion 9 may be a method of fitting both of the opening and closing mechanism of the first portion 7 and the second portion 9 existing separately. According to this method, for example, after the specimen liquid sensor 3 is placed on the upper surface of the first portion 7, the second portion 8 is fitted on to the first portion 7 from above, so that the second portion 9 is brought into a closed state. Still alternatively, the upper surface of the first portion 7 and the lower surface of the second portion 9 can be brought into a closed state by inserting the specimen liquid sensor 3 between the upper surface of the first portion 7 and the lower surface of the second portion 9 in a state in which the upper surface of the first portion 7 and the lower surface of the second portion 8 are engaged with each other while the upper surface of the first portion 7 and the lower surface of the second portion 8 face each other.

Although the shape and the material of the first portion 7 and the second portion 9 are not particularly limited, the first portion 7 and the second portion 9 are preferably small and lightweight so that the user can carry the apparatus 1 easily, and, for example, the first portion 7 and the second portion 9 are preferably made of resin such as polyethylene terephthalate (PET).

Figure 3B:
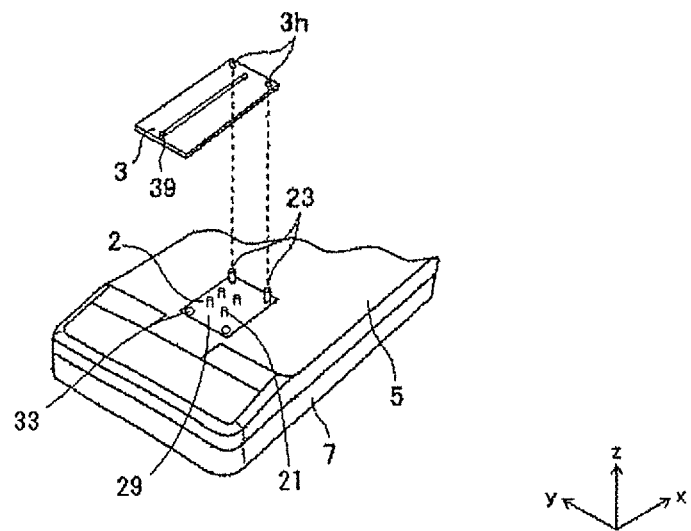
Figure 4:
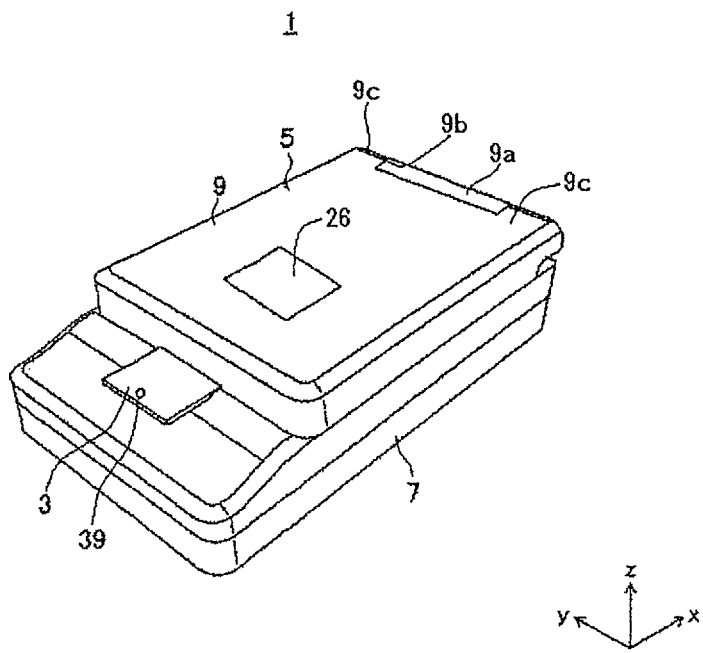
FIG. 4 is a perspective view illustrating the closed state of the specimen liquid sensor apparatus of FIG. 3.

As shown in FIG. 3(b), the first portion 7 may have a connection component 2 to electrically connect the specimen liquid sensor 3 and the reader 5 for positioning and fixing the specimen liquid sensor 3.

The positioning pin 23 protrudes from the upper surface of the first portion 7. This positioning pin 23 is provided on the first portion as a connection component 2, but the positioning pin 23 may be integrally formed with, for example, the first portion 7. In the present embodiment, two positioning pins 23 having a circular cross section are provided, but the present invention is not limited thereto, and the number, the arrangement position, the sectional shape, the diameter, and the height of the positioning pins 23 may be appropriately set.

On the other hand, in the specimen liquid sensor 3, a positioning hole 3h into which the positioning pin 23 is fitted is formed. In the specimen liquid sensor 3, the positioning pin 23 is fitted in the positioning hole 3h, so that the specimen liquid sensor 3 is positioned with respect to the first portion 7 in the direction along the x-y plane (the plane direction along the surfaces of the first portion 7 and the second portion 9 facing each other in the closed state).

Alternatively, in contrast to the above, a downward positioning pin may be provided with the specimen liquid sensor 3 and a positioning hole may be provided on the opposing surface of the first portion 7.

Figure 5:
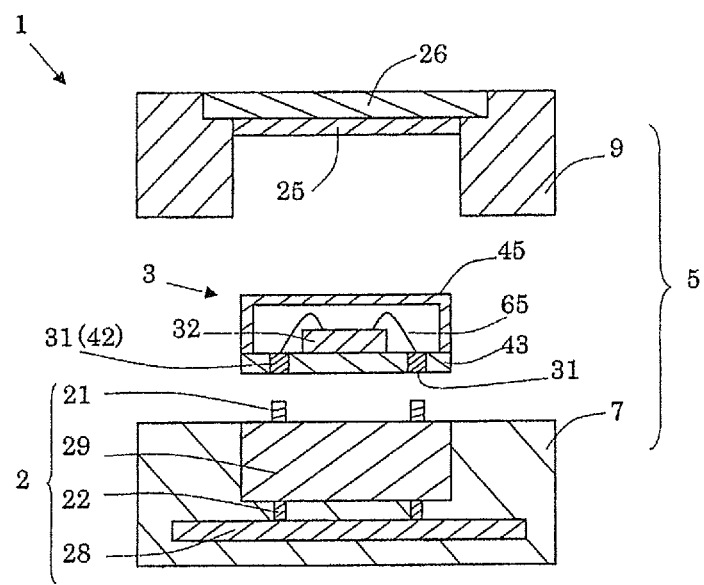
FIG. 5 is a schematic cross-sectional view illustrating the specimen liquid sensor apparatus of FIG. 4 including the specimen liquid sensor illustrated in the cross section taken along line A-A in FIG. 1.

As shown in FIG. 5, the terminal holding member 29 has a plurality of connection terminals 21 in the upper portion and a circuit terminal 22 connected to the circuit board 28 in the lower portion. The terminal holding member 29 is fixed to the upper surface of the first portion 7 with screws 33 as shown in FIG. 3(b).

The terminal holding member 29 is formed in a generally plate shape as a whole, for example. The wire of the terminal holding member 29 is connected, for example, via an opening formed in the first portion 7 by means of a signal line and a connector formed of an FPC or the like arranged inside the first portion 7.

As shown in FIG. 5, the first portion 7 further has a circuit board 28 below the terminal holding member 29 as shown in FIG. 5. The circuit board 28 and the terminal holding member 29 are connected by the circuit terminal 22. This circuit board 28 detects data of specimen liquid with regard to detection of data of the specimen liquid and transmits and receives this data to and from an external device or the like.

The terminal holding member 29 is fixed to the upper surface of the first portion 7 with the screw 33 and exposed to the outside in the open state of the reader 5.

As shown in FIG. 3(a), the reader 5 may have a temperature adjusting unit 25 capable of at least one of heating and cooling of the specimen liquid sensor 3 in the lower surface of the second portion 9. The temperature adjusting unit 25 is a member including a thermoelectric conversion element such as, for example, Peltier element. The Peltier element has, for example, a semiconductor, electrodes disposed on both sides of the semiconductor, and heat dissipation plates disposed on both sides of the semiconductor.

The temperature adjusting unit 25 may have a display unit 26 on the upper surface (the surface opposite to the first portion 7) in the second portion 9 (FIG. 4). The display unit 26 is preferably arranged adjacent to the temperature adjusting unit 25 so as to be able to exchange heat therewith, and the display unit 26 is preferably mounted on the surface of the second portion 9 so that the user can visually recognize the display unit 26. As this display unit 26, for example, the liquid crystal display unit and the like can be mentioned. The display unit 26 displays data detected by the specimen liquid sensor 3 from the specimen liquid. The display unit 26 is adjacent to the cooling surface side of the temperature adjusting unit 25, so that the heat generated by the operation of the display unit 26 can be cooled.

Figure 6:
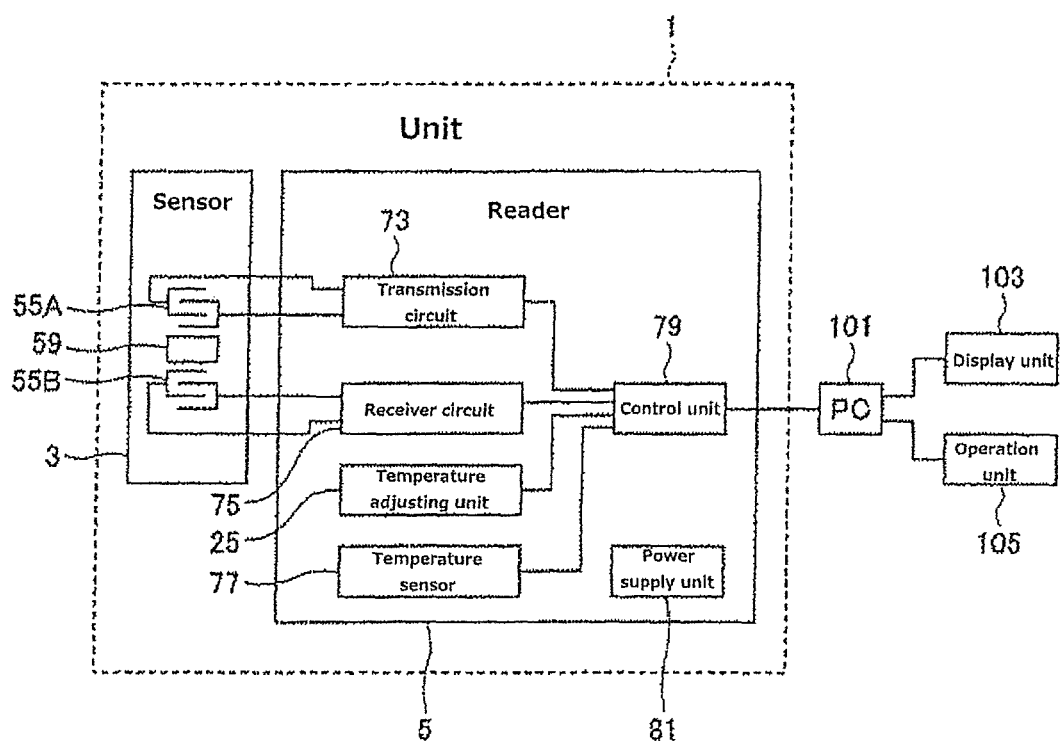
FIG. 6 is a block diagram illustrating the configuration of the signal processing system of the specimen liquid sensor.

FIG. 6 is a block diagram illustrating the configuration of the signal processing system of apparatus 1. The apparatus 1 (the reader 5) is used by being connected to a personal computer (PC) 101, for example. Although not specifically shown, for the connection with the PC 101, a connector based on a predetermined standard is appropriately provided in the reader 5. The PC 101 is connected to the interface such as, for example, the display unit 103 and the operation unit 105. It should be noted that the display unit 103 and the operation unit 105 may constitute a touch panel.

For example, the PC 101 displays information prompting the user to perform operation on the display unit 103, and outputs a control signal to the reader 5 based on the user operation with the operation unit 105. According to the control signal from the PC 101, the reader 5 inputs an electric signal to the specimen liquid sensor 3. The reader 5 performs appropriate processing such as amplification, filtering, or AD conversion on the electric signal output from the specimen liquid sensor 3, and outputs the processed electric signal to the PC 101. The PC 101 causes the display unit 103 to display the property or component information about the specimen liquid based on the electric signal from the reader 5.

The reader 5 includes at least a transmission circuit 73 for generating an electric signal input to the first IDT 55A, a receiver circuit 75 for receiving an electric signal that is output from the second IDT 55B, a temperature adjusting unit 25 as described above, a temperature sensor 77, a control unit 79 for carrying out these controls and the like, and a power supply unit 81 for supplying power thereto.

For example, the transmission circuit 73 is constituted by an IC and the like and includes a high frequency circuit. The transmission circuit 73 generates an AC signal having a frequency and a voltage according to the signal from the control unit 79 and inputs the AC signal into the first IDT 55A.

The receiver circuit 75 is constituted by, for example, an IC, and the like, and includes an amplifier circuit, a filter, or an AD conversion circuit. The receiver circuit 75 performs appropriate processing on the electric signal output from the second IDT 55B and outputs the electric signal to the control unit 79.

The control unit 79 includes a CPU, a ROM, a RAM, and the like. The transmission circuit 73 and the receiver circuit 75 are driven based on the control signal from the PC 101. The control unit 79 performs feedback control of the temperature adjusting unit 25 so that the temperature detected by the temperature sensor 77 constituted by a contact type temperature sensor of a resistance type such as, for example, a thermistor converges to a predetermined target value. For example, the target value is input from the PC 101.

The power supply unit 81 includes an inverter or a converter and converts the power from the commercial power supply or the PC 101 into an appropriate voltage, and supplies the power to the transmission circuit 73, the receiver circuit 75, the temperature adjusting unit 25, the temperature sensor 77 and the control unit 79.

The temperature sensor 77 may be provided. This temperature sensor 77 is constituted by a contact type temperature sensor of a resistance type such as, for example, a thermistor, and is provided in the vicinity of the position where the specimen liquid sensor 3 is placed, and an electric signal corresponding to the surrounding temperature is output to the control unit 79.

In the present embodiment, the external terminal 31 is provided on the lower surface side (at the first portion 7 side) of the specimen liquid sensor 3, but the present invention is not limited to such arrangement, and for example, the external terminal may be formed on the upper surface side of the specimen liquid sensor 3 (at the second portion 9 side) so as to come into contact with the connection terminal provided on the lower surface of the second portion 9. Alternatively, the external terminal may be formed on the side surface of the specimen liquid sensor 3 so as to come into contact with the connection terminal provided in the first portion 7 or the second portion 9.

<Measurement Method of Specimen Liquid>

Subsequently, a method for measuring a particular detection target contained in a specimen liquid using the apparatus 1 equipped with the specimen liquid sensor 3 will be described.

Figure 7A:
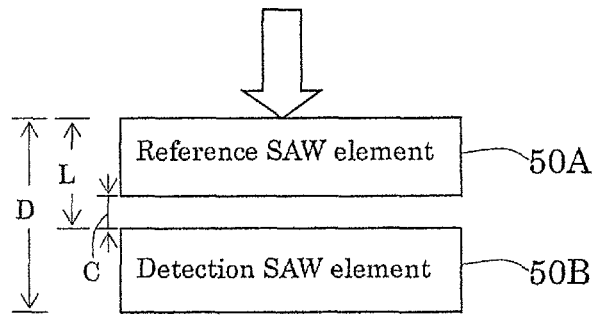
FIG. 7(a) is a block diagram illustrating an arrangement example of a reference SAW element and a detection SAW element in the specimen liquid sensor.

FIG. 7(*a*) shows that the specimen liquid is passed through the reference SAW element 50A and the detection SAW element 50B in this order in a direction indicated with an arrow in the embodiment shown in FIG. 2. In this case, as described above, the reference SAW element 50A and the detection SAW element 50B have the relationship of the expression: $t \cdot V < L$ (where t denotes a data reading interval time from both of the SAW elements, V denotes a flow rate of the specimen liquid, and L denotes a distance between both of the SAW elements).

In this case, the data reading interval time t from both of the SAW elements 50A and 50B can be set by the control unit 79 in the reader 5 with the operation of the operation unit 105.

Since the specimen liquid flows between the base 43 and the cover 45 with capillary action, the flow rate V of the specimen liquid can be adjusted by adjusting the height (thickness, z direction) in the flow path 35.

The position where the flow rate V of the specimen liquid is measured may be, for example, within the region denoted by reference symbol D in FIG. 7(*a*). More specifically, it is within the region from the upstream end of the reference SAW element 50A that the specimen liquid first reaches and the downstream end of the next detection SAW element 50B. Examples of measurements of the flow rate V include a method to measure the distance for which the specimen liquid flows within a given time through photographing with a high-speed camera, a method for measuring the time it takes for the specimen liquid to flow over a given distance, a deriving method for dividing the flow rate flowing from the downstream side of the detection SAW element 50B by the cross-sectional product of the flow path, and the like, and the measurement of the flow rate V is not particularly limited.

As shown in FIG. 7(*a*), the distance L of both of the SAW elements 50A, 50B is a distance from one end which is an end portion of the SAW element 50A which is one of the SAW elements and which is located at the upstream side of the flow of the specimen liquid to one end which is an end portion of the SAW element 50B which is the other of the SAW elements and which is also located at the upstream side.

In this case, in the case of the SAW elements 50A, 50B shown in FIG. 2, for example, one end of the SAW elements 50A, 50B may be a portion at the upstream side of one end (upstream end) of the sensitive part 59 to which the specimen liquid comes into contact and one end (upstream end) of the IDTs 55 (the first IDT 55A and the second IDT 55B).

As shown in FIG. 7(*a*), when the specimen liquid flowing in the flow path 35 reaches the surface of the sensitive part 59 of the SAW elements 50A and 50B, mass is added to the sensitive part 59. As a result, the phase θ of the SAW propagating from the first IDT 55A to the second IDT 55B is delayed to be changed into negative.

FIG. 7(*b*) illustrates an example of changes over time in the phase θref of the reference SAW element 50A and the phase θtest of the detection SAW element 50B. FIG. 7(*c*) illustrates an example of changes over time of the phase difference Δθ (θref-θtest) between θref and θtest. Each step (1) to (5) shown in the same figure will be explained. It should be noted that areas indicated by steps (1) to (5) are schematically indicated by arrows in FIG. 8.

step (1): This is the initial state in which the specimen liquid has not reached any of the reference SAW element 50A and the detection SAW element 50B. In this step, there is no mass applied to the SAW element, and therefore, none of θref and θtest has changed (θref=θtest=0). Therefore, there is no change in the phase difference Δθ, either.

step (2): This is a state from when the specimen liquid reaches the upstream end of the reference SAW element 50A to when the specimen liquid reaches the downstream end of the reference SAW element 50A. In this step, since the mass of the specimen liquid is applied to the reference SAW element 50A, θref changes to negative, but since the mass of the specimen liquid is not applied to the detection SAW element 50B, there is no change in θtest. Therefore, the phase difference Δθ changes to negative.

step (3): This is a state from when the specimen liquid passes through the reference SAW element 50A to when the specimen liquid passes through a clearance C between the reference SAW element 50A and the detection SAW element 50B. In this step, the specimen liquid has not reached the detection SAW element 50B, and the mass of the specimen liquid applied to the reference SAW element 50A has reached a maximum (the entire upper surface of the reference SAW element 50A is covered with the specimen liquid), and there is no change in θref. Therefore, in a time region between a point in time (A) when the application of the mass of the specimen liquid to the reference SAW element 50A has reached a maximum and a point in time (B) when the mass of the specimen liquid is applied to the detection SAW element 50B, the phase difference Δθ attains a minimum value P (extreme value).

step (4): This is a step from when the specimen liquid reaches the upstream end of the detection SAW element 50B to when the specimen liquid reaches the downstream end of the detection SAW element 50B. In this step, since the application of the mass of the specimen liquid to the reference SAW element 50A has reached the maximum due to the continuous influx of specimen liquid, θref has not substantially changed. On the other hand, since the mass of the specimen liquid is applied to the detection SAW element 50B, θtest changes to negative, so the phase difference Δθ changes to positive. Then, the specimen liquid further flows in, and when the addition of the mass of the specimen liquid to the detection SAW element 50B reaches the maximum, the phase difference Δθ becomes 0.

step (5): This is similar to step (4) explained above, and this is a state in which the application of the mass due to the inflow of the specimen liquid to the detection SAW element 50B has reached the maximum, and further, bonding reaction is performed between the detection target (receptor) in the specimen liquid and the specific bonding substance. In this step, since the mass of the receptor is applied in addition to the mass of the specimen liquid, the phase θtest in the detection SAW element 50B changes to negative more greatly than the phase θref in the reference SAW element 50A. Therefore, the phase difference Δθ changes to positive.

Even after the application of the mass due to the inflow of specimen liquid into the detection SAW element 50B reaches the maximum, the specimen liquid may continuously or intermittently flow out from the downstream end of the detection SAW element 50B. Alternatively, the flow of specimen liquid may be stopped at the point in time at which the application of the mass due to the inflow of the specimen liquid into the detection SAW element 50B has reached the maximum. In either case, as long as the bonding reaction continues between the detection target (receptor) in the specimen liquid and the specific bonding substance in the detection SAW element 50B, the phase difference Δθ in step (5) continues to change. Thereafter, at the point in time when the above bonding reaction in the detection SAW element 50B reaches saturation, the phase difference Δθ becomes a constant value.

In this case, the concentration of the detection target in the specimen liquid, which is the above-described receptor, is proportional to the bonding amount of the detection target to the specific bonding substance possessed by the detection SAW element 50B, i.e., the amount of negative change of θtest.

Figure 7B:
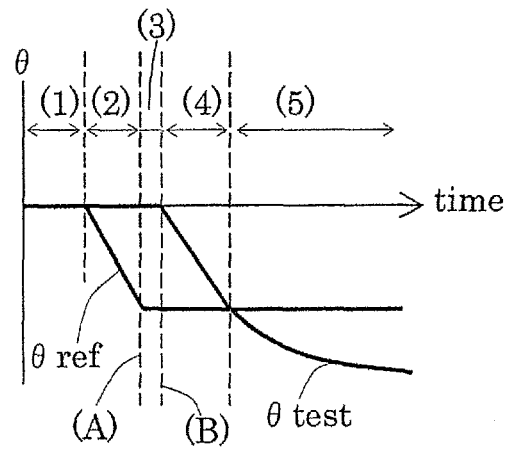
FIG. 7(b) is a graph illustrating an example of a phase $\theta$ref of SAW in the reference SAW element and phase $\theta$test of SAW in the detected SAW element in the arrangement example of FIG. 7(a).
Figure 7C:
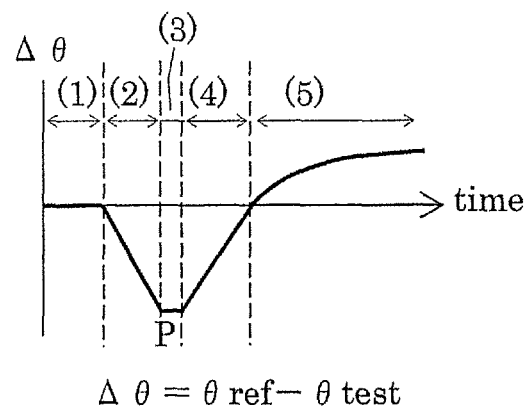
FIG. 7(c) is a graph illustrating a phase difference $\Delta\theta$ ($\theta$ref-$\theta$test) between $\theta$ref and $\theta$test illustrated in FIG. 7(b).
Figure 8:
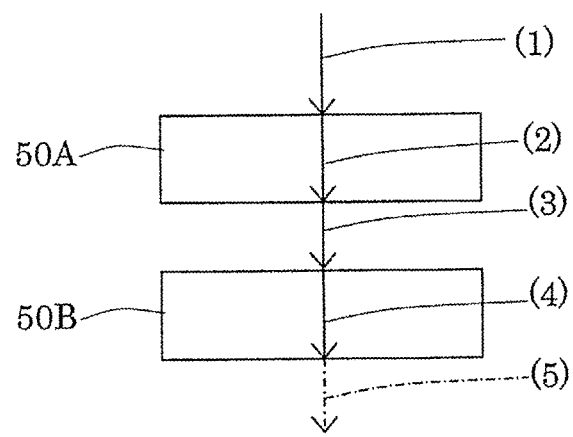
FIG. 8 is an explanatory view illustrating steps (1)-(5) illustrated in FIG. 7(b).
Figures 9A, 9B:
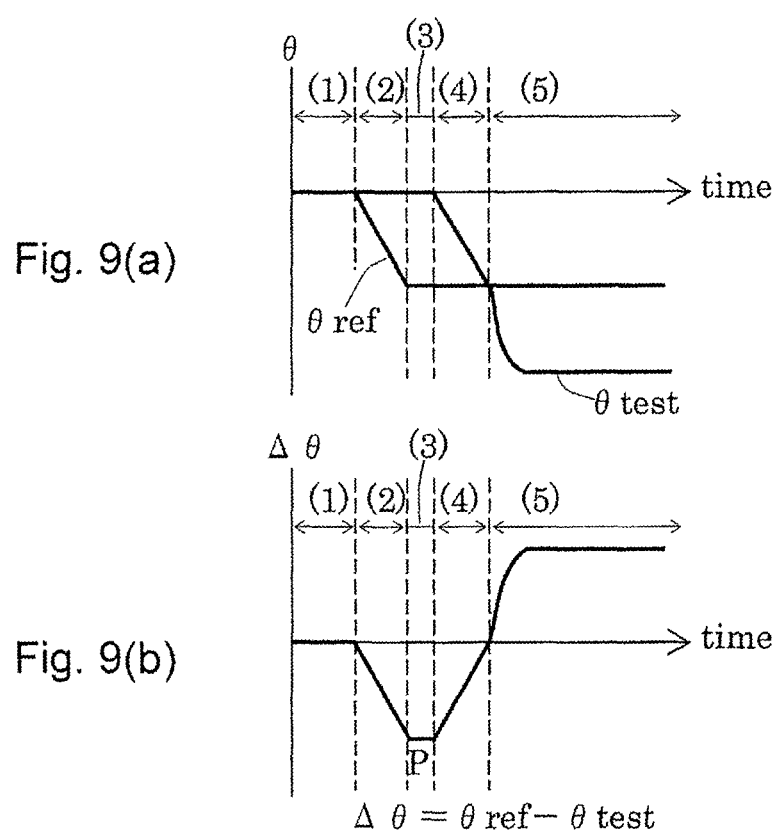
FIG. 9(a) is a graph illustrating the phase $\theta$ref of SAW in the reference SAW element and the phase $\theta$test of SAW in the detection SAW element in a case where, e.g., the detection target in the specimen liquid is contained at a higher concentration than the measurement in FIG. 7(b) or in a case where the density of the specific binding substances is high.
FIG. 9(b) is a graph illustrating a phase difference Δθ (θref-θtest) between θref and θtest illustrated in FIG. 9(a).

For example, when the concentration is higher than the concentration of the detection target in the specimen liquid shown in FIG. 7(b) and FIG. 7(c), or when the concentration of the specific bonding substance is high, the negative change of θtest in step (5) is larger than the negative change of θtest shown in FIG. 7(b) as shown in FIGS. 9(a) and 9(b).

As shown in FIG. 7(c) and FIG. 9(b), the phase difference Δθ has a minimum value P (extreme value) at any given point in time. As is evident from FIG. 7(b) and FIG. 9(a), this minimum value P is the point at which the specimen liquid reaches the detection SAW element 50B and the mass of the specimen liquid is applied to the detection SAW element 50B.

The concentration and the like of the detection target in the specimen liquid can be determined by the bonding amount of the detection target with the specific bonding substance of the detection SAW element 50B. This bonding amount can be determined from the amount of change in the phase difference Δθ within a certain period of time, the slope of the phase difference Δθ at any given point in time, and the like. Therefore, the point in time at which the mass of the specimen liquid is applied to the detection SAW element 50B, i.e., the minimum value P of the phase difference Δθ or later, can be used as the starting point of the measurement of the detection target. In this case, "the minimum value P or later" can be appropriately selected according to the movement of the output signal, but "the minimum value P or later" may be after the minimum value P but before the point in time at which the phase difference Δθ returns back to a value close to the initial value before the introduction of the specimen liquid (for example, a point in time when the phase difference Δθ returns back to zero), or a point in time later than the point in time at which the phase difference Δθ returns back to a value close to the initial value may be adopted as the starting point. The measurement of the detection target is preferably started from the point in time at which the specimen liquid flows into the SAW element at the downstream side (the detection SAW element 50B in the present embodiment), and according to this, the signal change itself in the SAW element at the downstream side (the detection SAW element 50B in the present embodiment) can be accurately measured without substantially being affected by the signal by the SAW element at the upstream side (the reference SAW element 50A in the present embodiment). More specifically, in the detection side SAW element 50B at the downstream side, the signal change based on the bonding reaction occurring between the detection target in the specimen liquid and the specific bonding substance can be accurately measured.

As described above, in order to attain the extreme value (the maximum value or the minimum value) over the change with time of the phase difference Δθ, both of the SAW elements 50A, SOB may have the relationship of the expression: t·V<L. In contrast, when both of the SAW elements 50A, 50B do not have the relationship of the expression: t·V<L, the extreme value (the maximum value or the minimum value) cannot be attained, or is difficult to be attained.

In order to measure the concentration and the like of the detection target, for example, the change amount of the phase difference Δθ within the above-mentioned certain period of time, the slope of the phase difference Δθ at any given point in time, and the like are measured by using the specimen liquid including the detection target of the known concentration, and a calibration curve is generated in which this change amount or slope is the horizontal axis and the concentration of the detection target is the vertical axis.

Subsequently, for the actual specimen liquid, the change amount of the phase difference Δθ, the slope of the phase difference Δθ at any given point in time, and the like are measured, the concentration and the like of the detection target can be measured from the calibration curve.

Figure 10A:
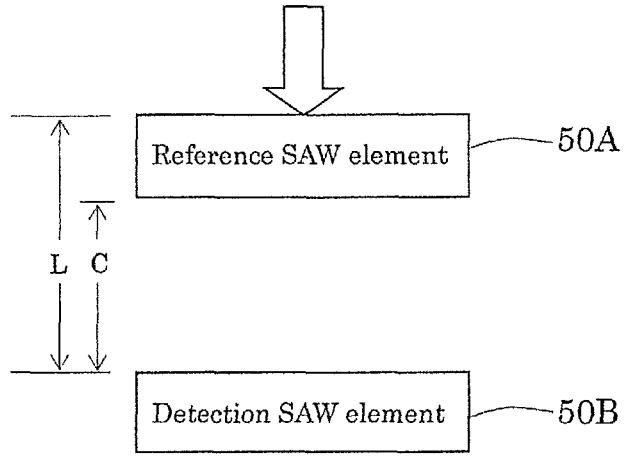
FIG. 10(a) is a block diagram illustrating an arrangement example of the reference SAW element and the detection SAW element in the specimen liquid sensor.
Figure 10B:
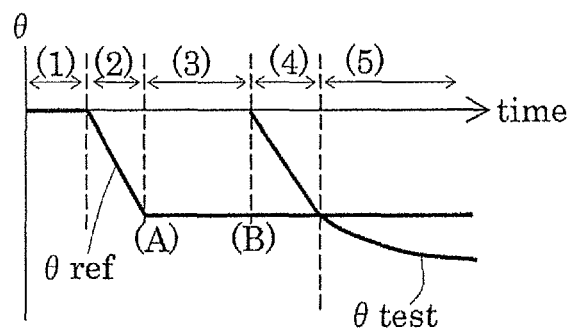
FIG. 10(b) is a graph illustrating another example of the SAW phase θref in the reference SAW element and the SAW phase θtest in the detection SAW element in the arrangement example of FIG. 10(a).
Figure 10C:
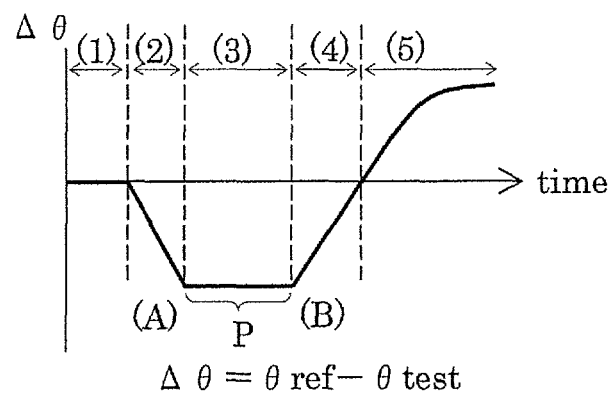
FIG. 10(c) is a graph illustrating the phase difference Δθ (θref-θtest) between θref and θtest illustrated in FIG. 10(b).

In FIG. 7(b), a point in time (A) at which the application of the mass of the specimen liquid to the reference SAW element 50A has reached the maximum and a point in time (B) at which the mass of the specimen liquid is applied to the detection SAW element 50B are relatively close to each other. On the other hand, in a case where the distance L of both of the SAW elements is large in the above equation (for example, as shown in FIG. 10(a), in a case where the interval C between both of the SAW elements 50A, 50B is large), the point in time (B) may emerge later than the point in time (A) as shown in FIG. 10(b). This can also happen when the flow rate V of the specimen liquid is small. In such a case, as shown in FIG. 10(c), the minimum value P has a constant time region. In the present embodiment, any point in time of the minimum value P having such a certain time region may be used as a starting point. This is because there is only a temporal shift between the case where the right end of the constant time region is the starting point and the case where the left end is the starting point. In FIGS. 10(b) and 10(c), (1) to (5) denote the steps shown in FIG. 8.

As described above, instead of causing the specimen liquid to flow through the reference SAW element 50A and the detection SAW element 50B in this order, the arrangement of the reference SAW element 50A and the detection SAW element 50B may be reversed so that the specimen liquid flows through the detection SAW element 50B and the reference SAW element 50A in this order.

In such arrangement, when a change with time of the phase difference Δθ(=θref-θtest) is calculated from the measurement values of θref and θtest, the maximum value (extreme value) emerges instead of the minimum value. Therefore, this maximum value or later may be adopted as the starting point of measurement of the detection target.

The SAW element is not limited to two, i.e., the reference SAW element 50A and the detection SAW element 50B. Three or more reference SAW elements and detection SAW elements may be arranged in the flow direction of the specimen liquid.

More specifically, for example, three or more SAW elements include at least one SAW element having a specific bonding substance bonding with the detection target included in the specimen liquid and at least another one SAW element having no specific bonding substance or having less specific bonding substances than the at least one SAW element. In the same manner as described above, three or more SAW elements may have specific bonding substances of types different from each other.

Of the three or more SAW elements, the SAW elements having the specific bonding substance may have different specific bonding substance densities or may have different specific bonding substances. In this case, when the densities of specific bonding substances are different in the plurality of SAW elements, the same detection target may be measured. When multiple SAW elements have different specific bonding substances, the multiple SAW elements may measure the same detection target or may measure different detection targets. For example, examples of different detection targets include RS, human meta, adeno, influenza, and the like. Multiple detection targets (virus) including the above can be measured at the same time.

Figure 11A:
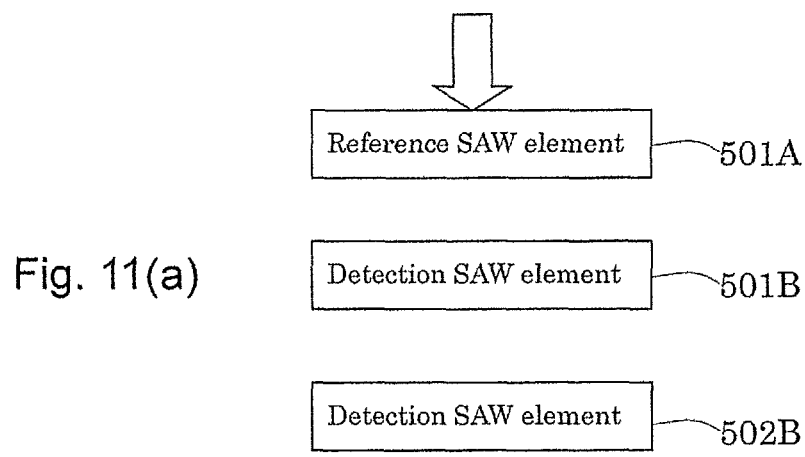
FIG. 11(a) and FIG. 11(b) are block diagrams illustrating examples in which three or more SAW elements are arranged.
Figure 11B:
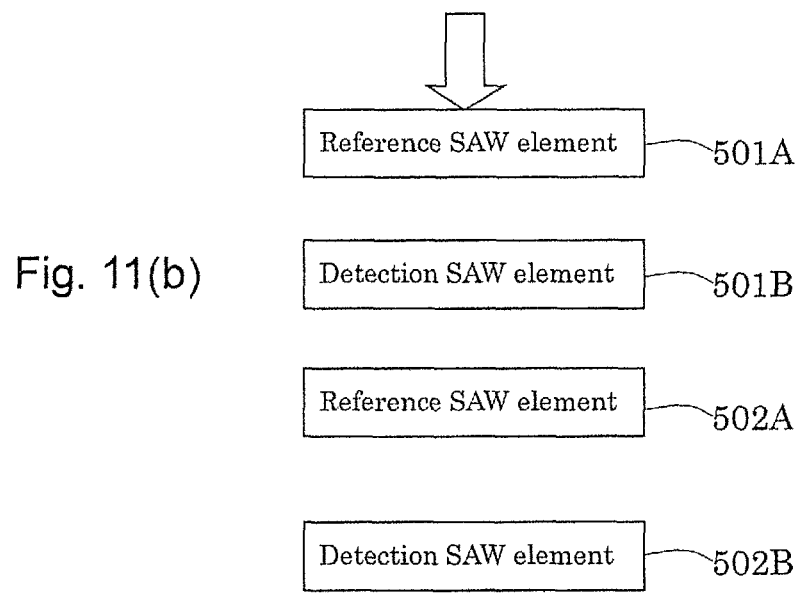

FIGS. 11(a) and 11(b) illustrate an example of arrangement of three or more SAW elements. In FIG. 11(a), in the flow direction of the specimen liquid as indicated by arrows, the reference SAW element 501A and the detection SAW elements 501B, 502B are arranged in this order. Two detection SAW elements 501B, 502B may have different densities of specific bonding substances or may have the same density of specific bonding substance. The detection SAW elements 501B, 502B may have different specific bonding substances.

In FIG. 11(b), in the flow direction of the specimen liquid as indicated by arrows, the reference SAW element 501A, the detection SAW element 501B, the reference SAW element 502A, and the detection SAW element 502B are arranged in this order. The reference SAW element and the detection SAW element may be aimed at different detection targets or may be aimed at the same detection target.

In the arrangement of the SAW elements as shown in FIGS. 11(a) and 11(b), the reference SAW element and the detection SAW element for measuring the detection target are required to have the relationship of the above expression: t·V<L, and as long as the reference SAW element and the detection SAW element for measuring the detection target are required to have the relationship, the interval L of adjacent SAW elements may be the same as each other or may be different from each other.

More specifically, for example, in FIG. 11(a), the reference SAW element 501A and the detection SAW element 501B have such relationship that they are positioned adjacent to each other, whereas the reference SAW element 501A and the detection SAW element 502B have such relationship that they are positioned not adjacent to each other. In any case, when configured to have the relationship of the above expression: t·V<L, the extreme value or later is adopted as the starting point of the signal from the specimen liquid sensor, and the detection target is measured by using the change with time after the starting point, so that the measurement (concentration measurement and the like) of the detection target contained in the specimen liquid can be performed easily and accurately, as described above.

In a case where multiple SAW elements have more than three SAW elements located with different distances, the SAW element may be configured to satisfy the relationship of the above expression: t·V<L in a similar manner.

As described above, according to the measurement method of the specimen liquid of the present embodiment, the reference SAW element and the detection SAW element have the relationship of the above equation. Therefore, in the difference between the phase θref of the surface acoustic wave in the reference SAW element and the phase θtest of the surface acoustic wave in the detection SAW element, i.e., the change with time of the phase difference Δθ, the extreme value (the maximum value or the minimum value) emerges. This extreme value represents the point in time at which the specimen liquid flowing through one SAW element reached the other SAW element. Therefore, the extreme value or later is adopted as the starting point of the signal from the specimen liquid sensor, and the detection target is measured by using the change with time at the extreme value or later, so that the measurement (concentration measurement and the like) of the detection target contained in the specimen liquid can be performed easily and accurately, as described above.

Other Embodiment

Figure 12:
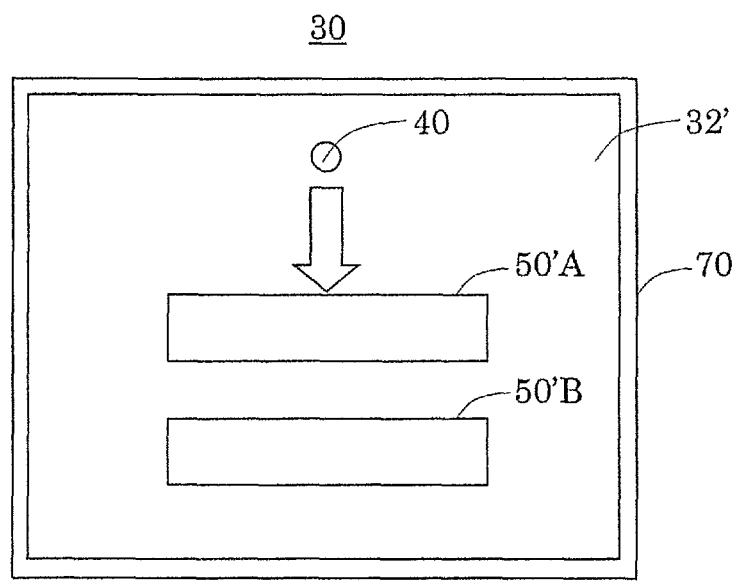
FIG. 12 is a schematic plan view showing a main part of a specimen liquid sensor according to another embodiment of the present invention.

FIG. 12 illustrates the specimen liquid sensor according to another embodiment of the present invention. This specimen liquid sensor 30 has a frame body 70 in which a sensor chip 32' surrounds a reference SAW element 50'A and a detection SAW element 50'B.

Unlike the previous embodiments, the specimen liquid sensor 30 does not have any flow path 35 which is formed between the base 43 and the cover 45 and through which the specimen liquid flows by using capillary action. Instead, the frame body 70 preventing the specimen liquid from flowing out is provided with the sensor chip 32'.

The frame body 70 is not particularly limited as long as the frame body 70 is a member capable of blocking the flow of the specimen liquid. For example, the frame body 70 may be a resin material.

For example, the specimen liquid is dropped to a drop position 40 shown in FIG. 12. Then, the specimen liquid flows from the drop position 40 toward the reference SAW element 50'A and the detection SAW element 50'B, so that the specimen liquid flows into both of the SAW elements 50'A, 50'B in this order.

In order to cause the specimen liquid to flow from the drop position 40 as described above, for example, it is possible to employ methods such as inclining the sensor chip 32', using the surface tension of the surface of the sensor chip 32'.

In a similar manner to the above embodiments, the inflow of the specimen liquid may be in the order opposite to the above embodiment, so that the specimen liquid flows through the detection SAW element 50'B and then the reference SAW element 50'A. In a similar manner to the above embodiments, the specimen liquid may flow through three or more SAW elements in order.

The remaining features are the same as those of the above embodiments, and detailed description thereabout is omitted.

Figure 13:
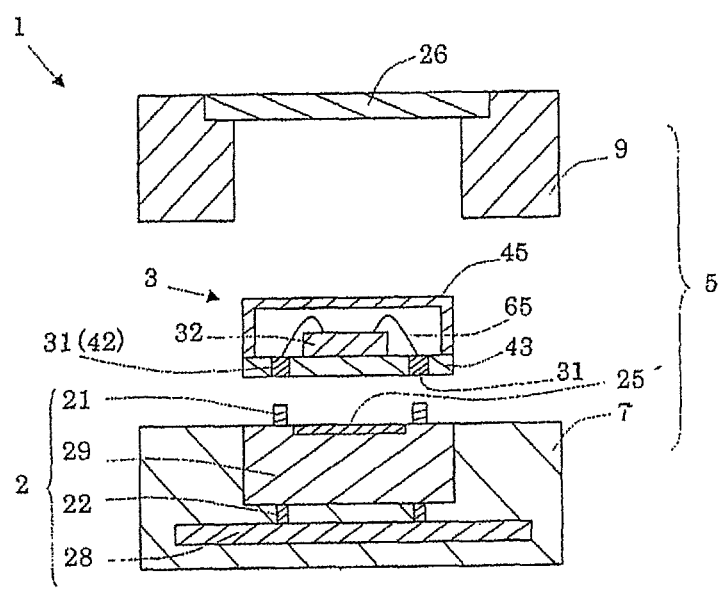
FIG. 13 is a schematic cross-sectional view illustrating a specimen liquid sensor according to still another embodiment of the present invention.

The present invention is not limited to the above embodiments, and various modifications and improvements are possible. For example, in the above embodiments, although the temperature adjusting unit 25 is provided in the second portion 9 of the reader 5, but alternatively, the temperature adjusting unit 25 may be provided in the first portion 7. As shown in FIG. 13, the temperature adjusting unit 25' may be provided in the area between a pair of connection terminals 21, 21 on the upper surface of the first portion 7. According to this configuration, the main constituent element is provided in the first portion 7 of the reader 5, and the electric circuit can be made with a simple configuration in the second part 9 of the reader 5.

Figure 14:
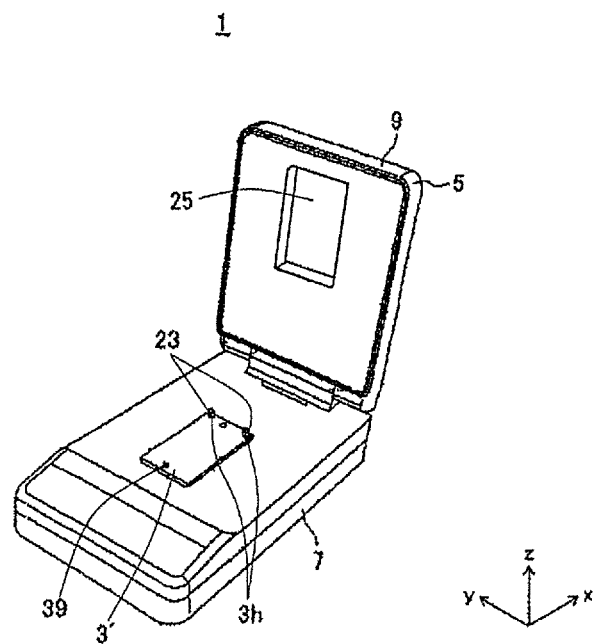
FIG. 14 is a perspective view illustrating a specimen liquid sensor apparatus according to still another embodiment of the present invention.

As shown in FIG. 14, the specimen liquid sensor 3' may be mounted inside of the reader 5 so that the specimen liquid sensor 3' is not exposed to the outside in the closed state of the reader 5. According to this configuration, the influence of external environment such as electromagnetic waves can be alleviated at the time of measurement.

In the above embodiments, a configuration in which no special member is provided inside of the flow path 35 has been explained. Alternatively, a porous member may be provided in a part or all of the inside of the flow path 35. According to this configuration, the flow rate of the specimen liquid flowing inside of the flow path 35 can be controlled. For example, when a porous member is provided in a part of the inside of the flow path 35, the porous member and the SAW element 50 may be in contact with each other.

DESCRIPTION OF THE REFERENCE NUMERAL

1: Specimen liquid sensor apparatus
2: Connection component
3, 30: Specimen liquid sensor
5: Reader
7: First portion
9: Second portion
21: Connection terminal
23: Positioning pin
25: Temperature adjusting unit
26: Display unit
29: Terminal holding member
31: External terminal
32: Sensor chip
35: Flow path
42: Through hole
43: Base
49: Conductor
50A, 50'A: Reference SAW element
50B, 50'B: Detection SAW element
70: Frame body
C: Clearance
L: Distance

The invention claimed is:

1. A measurement method of a specimen liquid, comprising:
preparing a sensor chip comprising a plurality of SAW elements located along a flow direction of the specimen liquid on an upper surface of a piezoelectric substrate, wherein a reference SAW element and a detection SAW element of the plurality of SAW elements have a relationship of an expression: $t \cdot V < L$, where t denotes a data reading interval time from both of the SAW elements, V denotes a flow rate of the specimen liquid, and L denotes a distance between upstream ends of the SAW elements;
causing the specimen liquid to flow in order from either one of the reference SAW element and the detection SAW element;
calculating a phase difference $\Delta\theta$ as a function of time while the specimen liquid is flowing, wherein the phase difference $\Delta\theta$ is equal to a difference between a phase $\theta$ref of a surface acoustic wave in the reference SAW element and a phase $\theta$test of a surface acoustic wave in the detection SAW element; and
measuring a detection target in the specimen liquid, wherein the measuring occurs at a point in time when the phase difference $\Delta\theta$ is at an extreme value, or later.

2. The measurement method of the specimen liquid according to claim 1, wherein
the detection SAW element has a specific bonding substance specifically bonding with the detection target included in the specimen liquid, and
the reference SAW element does not have the specific bonding substance, or has a lower density of the specific bonding substance than the detection SAW element.

3. The measurement method of the specimen liquid according to claim 1, further comprising:
measuring a change with time of the phase $\theta$ref; and
measuring a change with time of the phase $\theta$test.

4. The measurement method of the specimen liquid according to claim 1, wherein the specimen liquid is caused to flow in the order of the reference SAW element and the detection SAW element.

5. The measurement method of the specimen liquid according to claim 1, wherein
each of the reference SAW element and the detection SAW element comprises a first IDT electrode, a second IDT electrode located in a propagation path of a surface acoustic wave excited by the first IDT electrode, and a sensitive part located between the first IDT electrode and the second IDT electrode, and
the specimen liquid is caused to flow to the sensitive part of the reference SAW element and the sensitive part of the detection SAW element.

6. The measurement method of the specimen liquid according to claim 1,
wherein the sensor chip further comprises a flow path in which the specimen liquid flows and in which the reference SAW element and the detection SAW element are located in the flow direction, and
further comprising a step of causing the specimen liquid to flow from an upstream side of both of the reference SAW element and the detection SAW element in the flow path.

7. The measurement method of the specimen liquid according to claim 1,
wherein the sensor chip further comprises a frame body surrounding the reference SAW element and the detection SAW element,
further comprising a step of causing the specimen liquid to flow from one side of the reference SAW element and the detection SAW element toward the other side thereof in the inside of the frame body.

8. The measurement method of the specimen liquid according to claim 1, wherein the measurement of the detection target is performed in such a manner that a point in time, which the phase difference $\Delta\theta$ returns from the extreme value to zero, is the starting point.

* * * * *